United States Patent [19]

Jocewicz, Jr.

[11] Patent Number: 5,411,618
[45] Date of Patent: May 2, 1995

[54] METHOD AND APPARATUS FOR PRODUCING WAISTBAND-EQUIPPED DISPOSABLE DIAPERS

[75] Inventor: Frank F. Jocewicz, Jr., Green Bay, Wis.

[73] Assignee: Paper Converting Machine Company, Green Bay, Wis.

[21] Appl. No.: 157,980

[22] Filed: Nov. 24, 1993

[51] Int. Cl.⁶ .................. A61F 13/15; B32B 31/10
[52] U.S. Cl. .................. 156/164; 156/229; 156/267; 156/269; 156/495; 156/496; 156/516; 156/552
[58] Field of Search .......... 156/160, 164, 229, 495, 156/496, 552, 267, 269, 516, 163; 604/385.2

[56] References Cited

U.S. PATENT DOCUMENTS

| | | |
|---|---|---|
| 4,523,969 | 6/1985 | Spencer . |
| 4,704,116 | 11/1987 | Enloe ........................... 604/385.2 |
| 4,822,435 | 4/1989 | Igaue et al. ................... 156/164 |
| 4,834,740 | 5/1989 | Suzuki et al. ................ 156/164 X |
| 4,917,695 | 4/1990 | Villez .......................... 156/164 X |
| 4,925,520 | 5/1990 | Beaudoin et al. . |
| 5,000,806 | 3/1991 | Merkatoris et al. . |
| 5,004,466 | 4/1991 | Uda et al. . |
| 5,044,052 | 9/1991 | Hertel et al. . |
| 5,064,489 | 11/1991 | Ujimoto et al. ............... 156/164 |
| 5,190,606 | 3/1993 | Merkatoris et al. . |
| 5,296,080 | 3/1994 | Merkatoris et al. .......... 156/164 X |
| 5,308,345 | 5/1994 | Herrin ........................ 156/164 X |

FOREIGN PATENT DOCUMENTS 9309739  5/1993  WIPO ........................ 604/385.2

Primary Examiner—Jeff H. Aftergut
Attorney, Agent, or Firm—Tilton, Fallon, Lungmus & Chestnut

[57] ABSTRACT

A method and apparatus for making diapers wherein spaced apart moisture pervious webs are applied to fluff pads and overlaid with a further moisture pervious web which permits further processing prior to adhesively sandwiching a waistband between the further web and an underlying moisture impervious web.

21 Claims, 1 Drawing Sheet

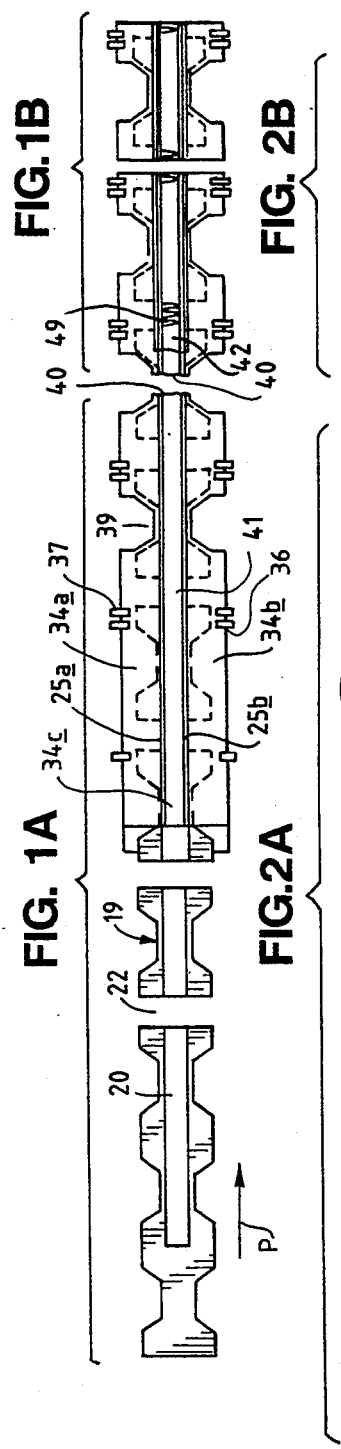
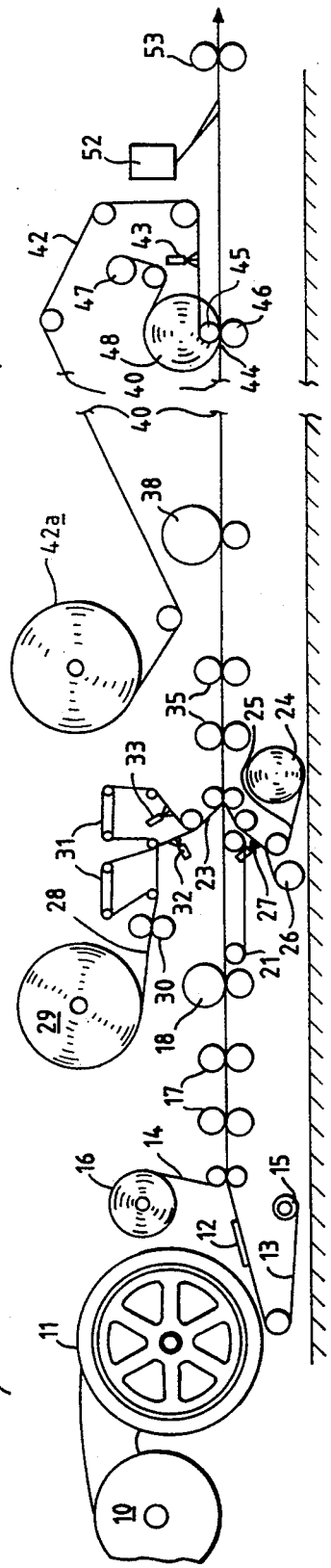
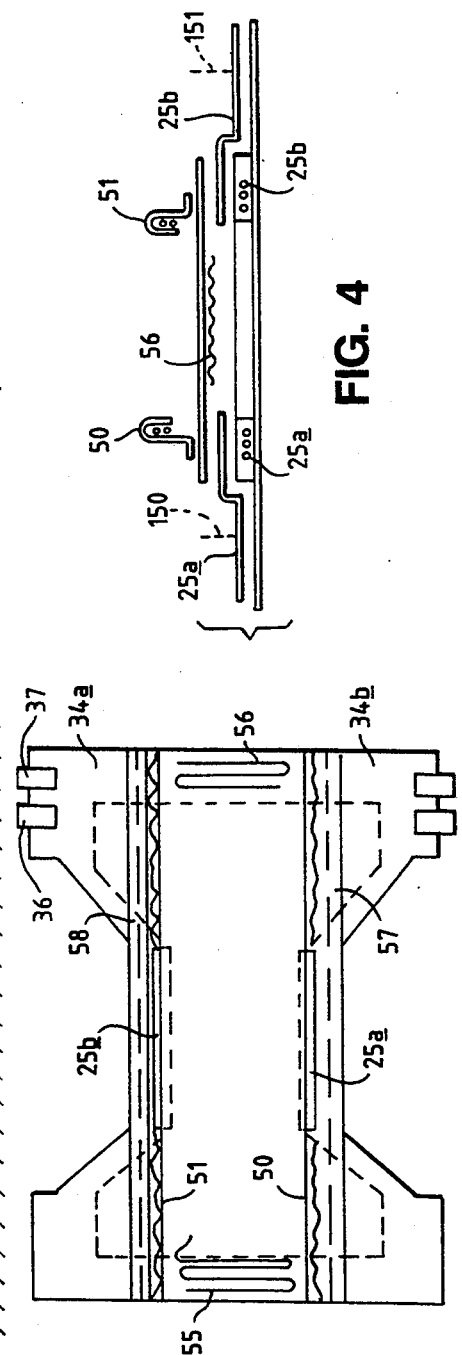

METHOD AND APPARATUS FOR PRODUCING WAISTBAND-EQUIPPED DISPOSABLE DIAPERS

BACKGROUND AND SUMMARY OF INVENTION

This invention relates to a method and apparatus for producing waistband-equipped disposable diapers and, more particularly, to a method and apparatus wherein the usual processing steps performed or normal features added without having to go to extraordinary lengths to maintain the waistbands in their original tensioned condition. This has been a problem especially in diapers of the adult brief variety where the waistbands are much larger and stronger than in the infant variety.

Waistband application in disposable diapers has been addressed in a number of prior art patents. Co-owned U.S. Pat. No. 4,523,969 proved successful in commercially producing adult diapers but with complicated machinery and processing. In the '969 patent and in U.S. Pat. No. 4,925,520 there were vacuum drums which were expensive to maintain.

Another prior art approach is seen in co-owned U.S. Pat. No. 5,000,806. This featured the diapers of the adult brief variety and which include a novel waistband construction and method of providing the same.

The prior art relating to waistbands can be seen in co-owned U.S. Pat. No. 5,000,806. This featured the application of an elastic strand manufactured by E. I. Du Pont de Nemours and Company marketed under the trademark Lycra. As Lycra can be stretched to levels exceeding 400%, it was difficult to obtain accurate placement of tapes or diecutting symmetry. This is overcome by the instant invention. Another prior art use of elastic waistbands is in U.S. Pat. No. 5,004,466 which employed a tape transfer step prior to adhesion to the poly-nonwoven substrates. The drawbacks of this method were high cost, unattractive tails visible through the material and the inability to control the placement.

Still further, the prior art procedure was the use of a single strand elastic aligned on a drum-type former system. This left red lines due to concentrated elastic force to the wearer and the diaper had to be held in vacuum to remain aligned which resulted in a costly method as well as the elastic having to be rotated before application.

The shortcomings of the prior art are overcome by the instant invention which employs a center position nonwoven web to sandwich waistband material between the bottom moisture impervious sheet and the center nonwoven material. More particularly, the invention provides for applying spaced-apart longitudinally-extending webs of non-woven, performing the usual processing steps such as leg cutout and tape tab application, and then applying the waistbands. Other objects and advantages of the invention may be seen in the details of the ensuing specification.

BRIEF DESCRIPTION OF DRAWING

The invention is described in conjunction with the accompanying drawing in which FIG. 1A is a schematic diagram of the first part of a diaper line including some teachings of the invention and as would be viewed essentially in top plan;

FIG. 1B is a view similar to FIG. 1A but constitutes a continuation thereof to illustrate the remaining teachings of the invention;

FIG. 2A is a schematic side elevational view of the equipment in a diaper manufacturing line which produces the diaper constructions seen in FIG. 1A;

FIG. 2B is a view similar to FIG. 2A and constitutes a continuation thereof so as to show the apparatus in the diaper line employed to develop the diaper configurations of FIG. 1B;

FIG. 3 is a top plan view of a diaper such as is constructed according to the instant invention and corresponds to the showing at the extreme right of FIG. 1B, but in greater detail; and FIG. 4 is a schematic end elevational view of the diaper construction of FIG. 3.

DETAILED DESCRIPTION

In the illustration given and with reference first to the PRIOR ART views FIGS. 1A and 2A, the numeral 10 at the extreme left of FIG. 2A designates a hammermill which shreds pulp to form fluff which is delivered to a drum former 11. Representative equipment of this nature can be seen in co-owned U.S. Pat. No. 5,044,052. Omitted from the drawing for clarity of presentation is the usual frame supporting the various pieces of apparatus but, in accordance with conventional practice, there are side frames which define a longitudinally extending path P.

The preformed fluff pad 12 comes off of the drum former and is sandwiched between two layers of tissue as at 13 and 14. The tissue webs forming layers 13 and 14 are derived respectively from parent rolls 15 and 16. In some cases the tissue wrapping may be omitted.

The thus-sandwiched pad is then sent through an embosser and debulker section 17 and then through the fluff pad cutoff 18. This results in a severed pad generally designated 19 and seen in the center portion of FIG. 1A. The showing to the left of the severed pad 19 illustrates the continuous stream of preformed pads and the envelopment thereof by the overlapped tissue as at 20.

Referring again to FIG. 2A, the numeral 21 designates a conveyor belt that is moving faster than the belt system prior to fluff pad cutoff and thus operates to separate the pads as illustrated at 22 in FIG. 1A. This upstream belt is omitted for ease of presentation.

The pads then move into a nip 23 where a continuous, full diaper width, moisture impervious sheet 25 (usually polyethylene) with leg elastic already attached) is adhered to the bottom of the pads 19. The poly web is derived from a parent roll 24 and the web 25 is equipped with the leg elastic from parent rolls 26 and adhesive applicator 27. The two leg elastics are illustrated in the central part of FIG. 1A as at 25a and 25b.

The Invention

In the same nip 23, nonwoven webs are applied to the pads. These are moisture-pervious and positioned next to the wearer's body. For this web purpose, a web of nonwoven material 28 is unwound from a parent roll 29 and is slit longitudinally by slitters 30. The slit webs are then separated by an edge guide separator 31 and adhered to the outer edges of the diaper by adhesive applied through nozzles 32, 33. The nonwoven webs are designated in FIG. 1A by the numerals 34a and 34b and are sized (transversely) to leave the center area 34c of the diaper covered only by the tissue 20.

In the prior art, the non-woven web was not slit and the waistband was applied prior to the application of the full width non-woven web—it being the practice to position the waistband between the full width plies of non-woven web and polyethylene web. Then, there was a problem in positioning and maintaining the waistband properly. And with a multiple strand waistband elastic, highly desirable in some instances, there was the further problem of achieving symmetry when die-cutting the configuration transversely.

From the nip forward, the continuous, multi-ply product is kept in constant tension in the machine direction, viz., the path P (see FIG. 1A). This keeps the diapers aligned for the steps following and the tension is to prevent the leg elastic from gathering. The diaper then moves into the tape applicator stations 35 resulting in tape tabs 36 and 37 on both sides of the continuous diaper web.

The continuous web now moves into the leg cutout station 38 which develops the cutout 39 illustrated at the right hand end portion of FIG. 1A. It has been found advantageous to perform these steps before the application of the waistband elastic because they apply stresses to the continuous web with longitudinally spaced waistbands that tends to disturb the requisite placement, tension, etc. Each of these further processing steps could be prejudiced should the waistband elastic—if present as in the prior art—contract and pull in the edges being worked on.

The first part of the inventive operation has been described in conjunction with FIGS. 1A and 2A and terminates essentially at the match line 40 at the extreme right. Now referring to FIGS. 1B and 2B, the match line 40 is again seen— but now at the extreme left in FIGS. 1B and 2B. The multiple ply diaper construction now moves into the final assembly stage. This includes first the provision of a center nonwoven web. This covers the exposed tissue 20 (if present) and, more importantly, the exposed areas of poly between pads as at 41). The center nonwoven 42 is derived from a parent roll 42a and is equipped with stripes of elastic via a nozzle 43. The web 42 of central nonwoven with the adhesive provided by the nozzle 43 enters a nip 44 provided by rolls 45 and 46.

Also entering the nip 44 is an elastic waistband which is derived from a parent roll 47 and applied via roll 48. The illustration here is that of co-owned U.S. Pat. No. 5,000,806 and operates in such a way as to sandwich the elastic 49 (see FIG. 1B) between the bottom poly sheet and the center nonwoven material (see FIG. 1B where the Lycra is in transversely sinusoidal form).

Thereafter, the diaper may be equipped with upstanding leg cuffs as at 50, 51 via cuff-providing station 52. A suitable arrangement for this purpose can be seen in co-owned U.S. Pat. No. 5,190,606.

Thereafter, the diaper continues to a cutter 53 which develops individual diapers as at 54. It will be noted that the cutter 53 severs the waistband material midway of its dimension in the machine direction. This leaves waistband portions 55 and 56 on adjacent diapers. Such an operation is useful not only with the Lycra material illustrated in FIG. 1B but also using a foam waistband or a film waistband.

This results in a diaper of the character illustrated in FIGS. 3 and 4. FIG. 3 is a plan view of the diaper and includes at the two ends the Lycra waistband 55, 56. It also includes the standing leg cuffs 50, 51 and fastening tapes 36, 37. The center non-woven ply 42 overlaps the side non-woven plies 34a, 34b in the longitudinal band areas 57, 58—see the lower part of FIG. 3.

The leg elastics are seen at 25a and 25b and the center base nonwoven is again designated 42—see also the left central portion of FIG. 1B. The center base nonwoven advantageously is hydrophilic whereas the outer nonwoven layers as at 34a and 34b are advantageously hydrophobic. Also it is within the scope of the invention to provide the two moisture pervious webs 34a, 34b and the center moisture pervious web 42 of colored material.

Reference to FIG. 4 shows many of the same elements, particularly the standing leg cuffs 50, 51. It is well within the scope of the invention to provide the leg cuffs in alternate positions—as on the outer nonwoven layers as at 150 and 151 (see FIG. 4).

While in the foregoing specification, a detailed description of an embodiment of the invention has been set down for the purpose of illustration, many variations in the details hereingiven may be made by those skilled in the art without departing from the spirit and scope of the invention.

I claim:

1. In a method of diaper manufacture, the steps of advancing a series of fluff pad along a linear path in longitudinally spaced relation, said pads having upper and lower faces, a pair of longitudinally extending sides, and a pair of transversely extending ends, uniting a continuous moisture impervious web to one face of said spaced pads to provide areas of exposed moisture impervious web between said spaced fluff pads, uniting two continuous moisture pervious webs to the other face of said spaced pads in laterally spaced relation to provide a longitudinally extending central area free of the moisture pervious webs while maintaining exposed the moisture impervious web areas between successive pads in said central area, performing at least one additional processing step on the pad united with the moisture impervious web and the two moisture pervious webs while such an assembly is advanced along the linear path, and adhesively sandwiching a transversely extending waist elastic between a further continuous web of moisture pervious material extending over each said central area and each said exposed moisture impervious web areas with said waist elastic being aligned with said exposed moisture impervious web areas.

2. The method of claim 1 in which said additional processing step includes the step of cutting longitudinal edges of each of said two continuous moisture pervious webs and longitudinal edges of said moisture impervious web to provide leg cutouts.

3. The method of claim 1 in which said steps include providing longitudinally extending leg cuff means on one of said central area web of moisture pervious material and said two moisture pervious webs.

4. The method of claim 3 in which said steps include providing a pair of transversely spaced leg cuffs on said central area web of moisture pervious material.

5. The method of claim 3 in which said steps include providing a longitudinally extending leg cuff on each of said laterally spaced moisture pervious webs.

6. The method of claim 1 in which said waist elastic is a strand and said steps include forming said strand into a plurality of transversely extending sinusoids.

7. The method of claim 1 in which said steps include providing a foam as said waist elastic.

8. The method of claim 1 in which said steps include providing film as said waist elastic.

9. The method of claim 1 in which said steps include providing said two moisture pervious webs of hydrophobic material and said further web of hydrophilic material.

10. The method of claim 1 in which said steps include providing said two moisture pervious webs and said further moisture pervious web of colored material.

11. The method of claim 1 in which said step include severing the product of said sandwiching by transversely cutting said product between successive fluff pads.

12. The method of claim 1 in which said steps include encasing said fluff pads in tissue.

13. In a method of diaper manufacture, the steps of advancing a series of fluff pads along a linear path in longitudinally spaced relation, said pads having upper and lower faces, a pair of longitudinally extending sides, and a pair of transversely extending ends, uniting a continuous moisture impervious web to one face of said spaced pads to provide areas of exposed moisture impervious web between said spaced fluff pads, uniting two continuous moisture pervious webs to the other face of said spaced pads in laterally spaced relation to provide a longitudinally extending central area free of the moisture pervious webs while maintaining exposed the moisture impervious web areas between successive pads in said central area, performing at least one additional processing step on the pad united with the moisture impervious web and the two moisture pervious web, and adhesively sandwiching a transversely extending waist elastic between a further continuous web of moisture pervious material extending over each said central area and each said exposed moisture impervious web areas with said waist elastic being aligned with said exposed moisture impervious web areas, said additional processing step including the step of applying tape tabs to the longitudinal edges of each of said two continuous moisture pervious webs.

14. Apparatus for diaper manufacture comprising a frame defining a linear path, means operably associated with said frame for advancing a series of fluff pads along said linear path in longitudinally spaced relation, said pads having upper and lower faces, a pair of longitudinally extending sides, and a pair of transversely extending ends, further means in said path for uniting a continuous moisture impervious web to one face of said spaced pads to provide areas of exposed moisture impervious web between said spaced fluff pads, means further in said path for uniting two continuous moisture impervious webs to the other face of said spaced pads in laterally spaced relation to provide a longitudinally extending central area free of the moisture impervious web areas between successive pads in said central area, means further in said path for performing an additional processing step on the spaced pads united with both moisture pervious webs and moisture impervious web while said advancing means advances the spaced pads united with both moisture pervious webs and moisture impervious web, and still further means in said path for adhesively sandwiching a transversely extending waist elastic between a continuous web of moisture pervious material extending over said central area and said exposed moisture impervious web areas with said waist elastic being aligned with said exposed moisture impervious web areas.

15. The apparatus of claim 14 in which said means for performing an additional processing step includes means for applying tape tabs to said spaced pads united with both moisture pervious webs and moisture impervious web.

16. The apparatus of claim 14 in which said means for performing an additional processing step includes means for cutting longitudinal edges of all of said united webs to provide leg cutouts.

17. The apparatus of claim 14 in which means are provided on said frame for providing longitudinally extending leg cuff means on one of said further web of moisture pervious material and said two moisture pervious webs.

18. The apparatus of claim 17 in which said leg cuff providing means are located adjacent said sandwiching means.

19. The apparatus of claim 17 in which said leg cuff providing means are located in alignment with said two moisture pervious webs.

20. The apparatus of claim 14 in which said apparatus includes further means for severing the product of said sandwiching by transversely cutting said product between successive fluff pads.

21. The apparatus of claim 14 in which said frame is equipped with means for slitting and aligning said moisture pervious webs to provide said central space.

* * * * *